United States Patent
Hsu et al.

(10) Patent No.: US 7,544,368 B2
(45) Date of Patent: Jun. 9, 2009

(54) STRUCTURE FOR MODULATING INTRAOCULAR PRESSURE

(75) Inventors: Wei-Cherng Hsu, Taipei (TW); Jo-Yi Hsiao, Tao Yuan (TW); Hsiao-Cheng Yen, Taichung (TW)

(73) Assignee: Life Spring Biotech Co., Ltd., Taipei (TW)

( * ) Notice: Subject to any disclaimer, the term of this patent is extended or adjusted under 35 U.S.C. 154(b) by 0 days.

(21) Appl. No.: 11/806,442

(22) Filed: May 31, 2007

(65) Prior Publication Data

US 2007/0292474 A1   Dec. 20, 2007

Related U.S. Application Data

(63) Continuation-in-part of application No. 11/471,695, filed on Jun. 21, 2006, which is a continuation-in-part of application No. 10/327,528, filed on Dec. 20, 2002, now abandoned.

(51) Int. Cl.
*A61F 2/00* (2006.01)
*A61K 38/17* (2006.01)
*C07K 1/00* (2006.01)

(52) U.S. Cl. .................. 424/427; 424/425; 424/428; 530/356; 530/364; 435/810

(58) Field of Classification Search .............. 424/427, 424/425, 428; 530/356, 364; 435/810
See application file for complete search history.

(56) References Cited

U.S. PATENT DOCUMENTS

| | | |
|---|---|---|
| 4,060,081 A | 11/1977 | Yannas et al. |
| 5,273,900 A | 12/1993 | Boyce |
| 5,489,304 A | 2/1996 | Orgill et al. |
| 5,629,191 A | 5/1997 | Cahn |
| 5,713,844 A | 2/1998 | Peyman |
| 5,743,868 A | 4/1998 | Brown et al. |
| 6,013,628 A | 1/2000 | Skubitz et al. |
| 6,063,116 A | 5/2000 | Kelleher |
| 6,218,360 B1 | 4/2001 | Cintron et al. |
| 6,299,895 B1 | 10/2001 | Hammang et al. |
| 2002/0090391 A1 | 7/2002 | Geistlich et al. |
| 2002/0123805 A1 | 9/2002 | Murray et al. |
| 2005/0147679 A1 | 7/2005 | Petito et al. |

OTHER PUBLICATIONS

Hsu et al. Inhibition of Conjuctival Scarring and Contraction by a Porous Collagen-Glycosaminoglycan Implant, Aug. 2000, Inv. Ophthalmol. Vis. Sci., vol. 41, No. 9, pp. 2404-2411.*
Yannas et al. Synthesis and characterization of a model extracellular matrix that induces partial regeneration of adult mammalian skin, Feb. 1989, Proc. Natl. Acad. Sci. USA, vol. 86, pp. 933-937.*
Doillon, C.J. et al., "A collagen-based scaffold for a tissue engineered human cornea: Physical and physiological properties," International Journal of Artificial Organs 26: 8, Milan, Italy, Aug. 1, 2003, pp. 764-773.
European Search Report dated Nov. 13, 2008, for European Application No. 08157329.7.
Berstrom et al., Arch Ophthalmol., 1991, 109:1725-1730.
Miller et al., Ophthalmic Surg., 1989, 20:350-357.
Peiffer et al., Glaucoma, 1981, 3:277-280.
Yannas et al., Science, 1982, 215:174-176.
Yannas IV, Wound Repair Regan., 1998, 6:518-524.
Orgill et al., Behavior of Collagen-GAG Matrices as Dermal Replacement in Rodent and Porcine Models, Sep./Oct. 1996, Wounds, vol. 8, No. 5, pp. 151-157.

* cited by examiner

*Primary Examiner*—Jon P Weber
*Assistant Examiner*—Abdel A Mohamed
(74) *Attorney, Agent, or Firm*—Venable LLP; Cameron H. Tousi; Matthew E. Kelley

(57) ABSTRACT

Embodiments of the present invention are directed to three-dimensional porous structures for modulating intraocular pressure. The structures can include a mixture of copolymers, for example, collagen and glycosaminoglycan.

12 Claims, 9 Drawing Sheets

STRUCTURE FOR MODULATING INTRAOCULAR PRESSURE

This is a continuation-in-part of application Ser. No. 11/471,695, filed Jun. 21, 2006, which is a continuation-in-part of application Ser. No. 10/327,528, filed Dec. 20, 2002, which is now abandoned, all of which are incorporated herein.

BACKGROUND OF THE INVENTION

1. Field of Invention

In some embodiments, the present invention generally relates to a drug-free biodegradable 3-dimentioned porous collagen-glycosaminoglycan scaffold serving as an implantation device, and in particular to a device designed for preventing scar formation and creating a physiological aqua buffer environment in conjunctival space for modulating the intraocular pressure on glaucoma.

2. Background

Glaucoma encompasses serial symptoms such as intraocular pressure elevation, optic nerve damage and progressive visual field loss. Most patients receive medical treatments by oral ingestion or locally applying beta-blockers, miotics, adrenergic agonists or carbonic anhydrase inhibitors to enhance water reabsorption by blood vessels and consequently lower the intraocular pressure. Most of the patients significantly respond to drug therapy at the beginning, but in many cases turn out to be refractory over time. For the individual who fails to quickly respond to drug treatment, surgical intervention is required in order to maintain intraocular pressure.

Glaucoma filtering surgery is the current operating process for reducing intraocular pressure. The processes of glaucoma filtering surgery consists of making an opening through the trabeculum to drain out aqueous humor from the anterior chamber, and building a filtering bleb or drainage fistula between the anterior chamber and the subconjunctival space to reduce intraocular pressure (Bergstrom et al., 1991; Miller et al., 1989). However, the scar development after surgery results in the obstruction of the built filtering bleb or drainage fistula and finally leads to the recurrence of high intraocular pressure (Peiffer et al., 1989). Hence, the prevention of scar formation should be an important consideration for the success of glaucoma surgery.

Clinical treatments use mitomycin-C, 5-fluorouracil, bleomycin, beta-aminopropionitrile, D-penicillamine, tissue plasminogen activator and corticosteroid for the inhibition of fibroblast proliferation to prevent scar development after glaucoma surgery. Nevertheless, observed side effects, such as thinning of the conjunctiva or intraocular inflammation can lead to blindness.

U.S. Pat. No. 5,713,844 and U.S. Pat. No. 5,743,868 disclosed pump- or tube-like devices made with artificial materials being implanted into the subconjunctival space or the anterior chamber surroundings as an alternative to the filtering bleb or drainage fistula to lower the intraocular pressure. These non-degradable devices function as the fistula and bleb, giving short-term benefits but the procedure eventually fails due to scar formation. Moreover, the devices are not biodegradable, causing incommodity and risk of secondary infection. In addition, no clinical observation shows significant reduction of scar formation after implanting such devices. As a matter of fact, the regenerative tissue often invades or pinches into the implanted devices, consequently obstructing the outflow pathway. For the most part, it is not a general therapeutic consideration.

For years, studies on tissue engineering achieved great progress in scar prevention (Yannas et al., 1989; Yannas, 1998). For example, artificial skin contributes great benefits to wound healing (Orgill et al., 1996; Yannas et al., 1982). U.S. Pat. No. 4,060,081 and U.S. Pat. No. 5,489,304 disclosed artificial skin to benefit wound healing and prevent scar formation. Both types of artificial skin combine a degradable layer and another non-degradable layer. The non-degradable layer composed of synthetic polymers controls moisture flux of the skin; and the degradable layer composed of a three-dimensioned (3D) collagen-mucopolysaccharide or collagen-glycosaminoglycan copolymer directly covers the wound area to support tissue regeneration. The 3D collagen-mucopolysaccharide or collagen-glycosaminoglycan copolymers lead a random reorganization of the regenerating fibroblasts and the secreted intercellular matrix, and finally result in a reduction of scar formation.

To mimic skin physiological function, some of the prior methods and devices have been designed with a high intensity of chemical linkage between components and functional control of the moisture flux. In addition, these products are generally for external application, rather than for use as an implanting device. It is not possible to apply such artificial skin as an implanting device directly in a glaucoma treatment. Another resolution for preventing scar formation and modulating intraocular pressure after glaucoma surgery is highly desirable.

U.S. Pat. No. 6,299,895 and U.S. Pat. No. 6,063,116 disclosed implanting devices, which carried different biological active molecules to inhibit cell proliferation, amend tissue regeneration and prevent scar development. However, the building components are not fully biodegradable. U.S. Pat. No. 6,013,628 and U.S. Pat. No. 6,218,360 presented a combination of cell proliferating inhibitors and different biodegradable mediators, and the direct application into the intraocular tissue. Although these patents addressed the problem of the non-degradability of the drug mediator, there is still the risk that the drug may leak out from the injecting site. The affected area will be beyond control. Moreover, such a biodegradable matrix does not function as a pressure regulator capable of modulating the intraocular pressure through a physical means, i.e., to modulate the pressure of the intraocular fluid by establishing a physiological aqua buffer reservoir.

Summary of the Invention

In some embodiments, the present invention provides a 3D porous collagen glucosaminoglycan scaffold, which is fully biodegradable after being implanted into the subconjuctival space. The 3D porous structure reduces intraocular pressure, leads a re-arrangement of proliferating cells and matrix, prevents scar formation, and provides a permanent physiological aqua reservoir system after biodegrading.

An object of the invention, in some embodiments, is to provide a new device for glaucoma implantation. In some preferred embodiments, there are provided methods of purifying type I collagen and making a biodegradable 3D porous collagen/glucosaminoglycan scaffold serving as an implanting device. The device leads to cell re-organization during regeneration and builds a physiological aqua buffer reservoir for the modulation of intraocular pressure (IOP) after glaucoma surgery. On the other hand, no further aldehyde linkage has been conducted during preparation procedures, and consequently reduces the hardness and the risk of chemical remnants.

A further object of the invention, in some embodiments, is to provide a special procedure of implanting the device into animals' subconjunctival space. No drug should be added during and after the implantation. The present invention prevents scar development and modulates the intraocular pressure based only on the 3D porous structure and the biodegraded residual space. The present invention is not used as a drug mediator or drug carrier.

In one embodiment, the intraocular pressure has been measured after implantation. In other embodiments, different cellular evaluations were also performed on the days 3, 7, 14, 21 and 28 after implantation, so as to monitor the scaffold biodegradation and the tissue regeneration.

The foregoing and other objects, features, aspects and advantages of the present invention will become better understood from a careful reading of a detailed description provided herein below with appropriate reference to the accompanying drawings.

BRIEF DESCRIPTION OF THE DRAWINGS

FIG. 2 shows the morphological-evaluation after scaffold implantation in female New Zealand albino rabbits.

FIG. 2A shows the immune-responded cells infiltrated into the cross-referred area of the implanted area (*). The scaffold was degraded partially and some regenerated cells invaded this area (.Arrow-up bold.). (H&E stain, 40×, Day 3).

FIG. 2B shows the immune-responded cells infiltrated into the cross-referred area of the operating sham groups (*). (H&E stain, 40×, Day 3).

FIG. 2C shows identified fibroblasts (.tangle-solidup.) and secreted collagen (.Arrow-up bold.) randomly arranged in the cross-referred area of the implanted area. (Masson Trichrome stain, 400×, Day 14).

FIG. 2D shows identified fibroblasts (.tangle-solidup.) and secreted collagen (.Arrow-up bold.) compactly arranged in the cross-referred area of the operating sham groups. (Masson Tricbrome stain, 400×, Day 14).

FIG. 2E shows very few α-SMA immuoreactive cells (.Arrow-up bold.) randomly appeared in the remaining area of degraded scaffold. (.alpha.-SMA immunocytochemistry, 400×, Day 14).

FIG. 2F shows numerous α-SMA immuoreactive cells (.Arrow-up bold.) compactly arranged in the cross-referred area of the operating sham groups. α-SMA immunocytochemistry, 400×, Day 14).

FIG. 2G shows very little identified collagen randomly distributed in the remaining area of fully degraded scaffold (.Arrow-up bold.). (Masson Trichrome stain, 2×, Day 28).

FIG. 2H shows typical scar tissue (.Arrow-up bold.) shown as compactly arranged collagen fibers distributed in the cross-referred area of the operating sham groups. (Masson Trichrome stain, 2×, Day 28).

DETAILED DESCRIPTION OF THE INVENTION

Figure 1:
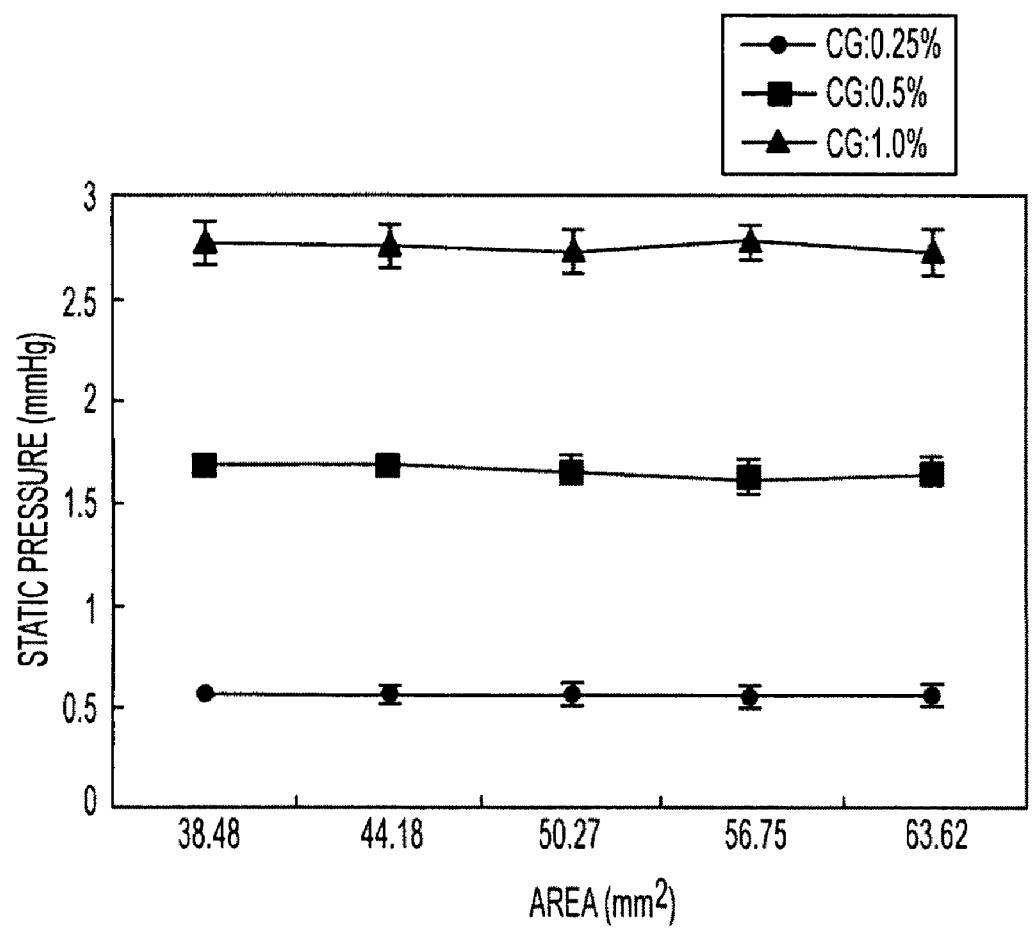
FIG. 1 shows the change of the static pressure of scaffolds in different concentrations of collagen-glycosaminoglycan.

In some embodiments, the present invention provides a fully biodegradable 3D porous scaffold, which is comprised of collagen-glucosaminoglycans copolymers. The terms "scaffold" or "collagen matrix" shall both mean a matrix comprised of collagen-glucosaminoglycans copolymers, or polymers that function in a similar manner to the polymers described below. Although numerous studies and patents described the use of collagen alone or in combination with other components as biomaterials, the present invention sets high temperature (see examples) and UV light as the major energy for polymerization, and non-obviously, no further aldehyde linkage reaction has been done through the preparation. Hence, there are no aldehyde remnants. As a result, the final product not only maintains the 3D porous structure to lead the regenerating tissue reorganization but also is softer in comparison to those disclosed in other prior arts (U.S. Pat. No. 5,629,191, U.S. Pat. No. 6,063,396, and Hsu et al., 2000). In addition, some embodiments of this invention provide a scaffold having the characteristics of the saturated statistic pressure and stiffness in desired ranges to allow the scaffold to act as 3D physiological aqua buffer reservoir which adjusts the intraocular fluid pressure and further reduces of the chance of adhesion in scleral tunnel before the wound has matured.

On the other hand, many other methods and devices provide implanting devices to be drug mediators or carriers, wherein the drugs released from mediators or carriers locally inhibit cell proliferation and prevent scar development. However, the drug re-filling is complicated and no side effects have been evaluated for certain drugs. The present invention thus offers a structure of modulating intraocular pressure on glaucoma as the resolution of these issues. The scaffold prevents scar formation by directly guiding the proliferating cells and matrix to scattered rearranging in its 3D porous structure. Consequently, the residual space after the scaffold being degraded is filled with loose connective tissue, and works as a permanent water reservoir to buffer intraocular pressure. The scaffold not only solves the recurrence of abnormal intraocular pressure but also eliminates the risk which might occur during drug loading and its side effects.

The saturated statistic pressure of the scaffold can increase according to the percentage of the copolymers used in the scaffold. Therefore, in some embodiments, the scaffold has a saturated statistic pressure of about 0.5 mmHg to about 5.5 mmHg. In other embodiments, the saturated static pressure is about 0.5 mmHg to about 5 mmHg, about 0.75 mmHg to about 4.75 mmHg, about 1 mmHg to about 4.5 mmHg, about 1.25 mmHg to about 4.25 mmHg, about 1.5 mmHg to about 4 mmHg, about 1.75 mmHg to about 3.75 mmHg, about 2 mmHg to about 3.5 mmHg, about 2.25 mmHg to about 3.25 mmHg, about 2.5 mmHg to about 3 mmHg or about 2.75 mmHg. As one of skill in the art will appreciate, there are many ways to vary the saturated static pressure of the scaffold, including for example, altering the percentage of collagen in the scaffold.

Figure 11:
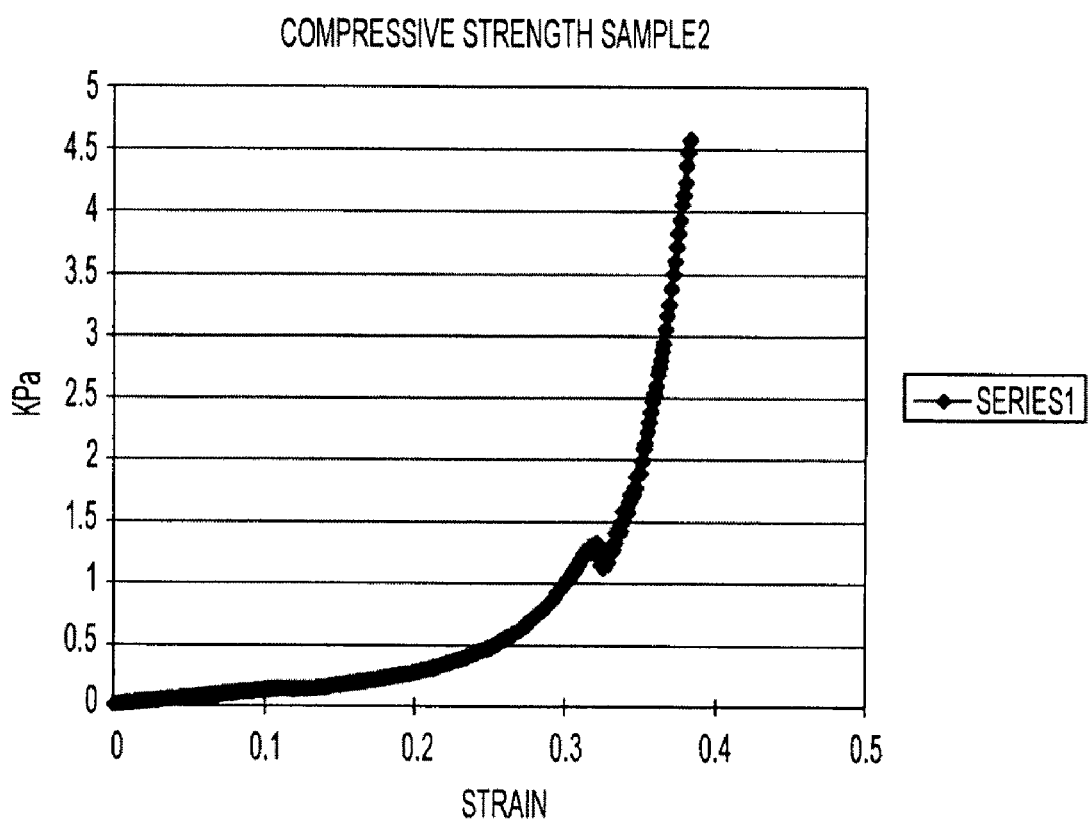
FIG. 11 shows the relationship between anti-compressive pressure and the strain of PBS soaked collagen matrix. The pressure elevated directly with the change of strain up until the point of 0.32 KPa.

The stiffness of the scaffold means the maximum pressure the scaffold can sustain without the occurrence of change in pressure which is of the pattern that a sudden drop of pressure appears and then a sudden elevation of pressure (FIG. 11). In some embodiments, the stiffness is between about 0.1 KPa to about 1.5 KPa:

|  | GAGs/Collagen | | | | |
| --- | --- | --- | --- | --- | --- |
|  | 1/6 | 1/12 | 1/24 | 1/48 | 1/96 |
| stiffness | 0.13 KPa | 0.51 KPa | 1.43 KPa | 0.46 KPa | 0.21 KPa |

However, since the scaffold should has a minimal physical strength in order to maintain its shape without collapsing after being implanting. It is preferred that the scaffold should have the stiffness of at least 0.5 KPa. In the more preferred embodiments, the stiffness is at least about 1 KPa, and, in the most preferred embodiments, the stiffness is at least about 1.4 KPa.

All above embodiments are made of collagen-glucosaminoglycans, and the scaffold made by gelatin which is similar to collagen, or other polymer or copolymers, should have such characteristics of saturated statistic pressure and stiffness if it is used as an implant for the treatment of glaucoma or as a coverage for the wound on eyes.

In some embodiments, the percentage of collagen-glycosaminoglycan copolymers in solution when producing the scaffold for use as a glaucoma implant ranges from about 0.125% to about 8% in acetic acid solution or water. The collagen can be type I collagen in some embodiments of the present invention.

The glycosaminoglycan can be, but is not limited to, one or more of the following: chondroitin-6-sulfate, chondrotin-4-sulfate, heparin, heparan sulfate, keratan sulfate, dermatan sulfate, chitin, chitosan, and mixtures thereof. The collagen can be, but is not limited to, a gelatin which is similar to collagen.

In some embodiments, type I collagen and the glycosaminoglycan can be crosslinked in a ratio of 6:1, 10:1, 12:1, 24:1, 48:1 or 96:1 (glycosaminoglycan:collagen) by weight through high temperature and being thoroughly mixed at a high speed. To maintain the scaffolds being softer than those being fabricated with an aldehyde linkage after being saturated with physiological phosphate buffered saline (PBS), there is no secondary aldehyde linkage during the preparation. Preferably, the scaffold should be kept dry until it is prepared for implantation.

In some embodiments, the scaffold has pores of a size ranging from about 10 μm to about 300 μm. The pore size can also be from about 20 μm to about 200 μm. In some embodiments, the pore size is measured after the scaffold has been saturated with saline, while in other embodiments the pore size is measured in a dry scaffold.

Some embodiments of the present invention apply to methods of using the scaffolds disclosed herein as part of glaucoma surgery. As shown in the examples below, collagen/glycosaminoglycan copolymers containing the ratio and size of the disclosed scaffold have been cut and saturated with physiological phosphate buffered saline. The surgeon may carefully dissect the conjunctiva from the formix to the limbus, and expose the sciera. The surgeon may make a trabecular channel connecting the subconjunctival space and the anterior chamber. Then, the surgeon may implant the PBS saturated scaffold into the subconjuctival space surrounding and above the sclera flap.

The PBS saturated scaffold provides a static pressure against the intraocular pressure to avoid excessive aqueous humor leaking out from the anterior chamber, and consequently prevents hypotony shortly after glaucoma surgery. Additionally, based on this physical effect and the location of implantation, the contact chance and time between scleral flap and bed can be reduced by the fluctuation of the difference of the pressure between intra-ocular pressure and static pressure. Because of that, the chance of adhesion in scleral tunnel can be reduced efficiently. The biodegradable 3D porous structure of the implanted scaffold provides a drug-free and chemical-free environment to lead to the rearrangement of the proliferating cells and matrix, and finally to prevent scar development. It results in a loose tissue structure after fully degrading. The loose structure then offers a permanently physiological aqueous humor buffer reservoir to modulate intraocular pressure.

The present invention, in some embodiments, is also directed to kits containing a scaffold described herein. Such a kit for the use in laser surgery on the eye may comprise the positioning marker such as the markers as disclosed in, but not limited to, those disclosed in U.S. Pat. Nos. 6,607,527 or 5,533,997.

The following examples are shown in the way of illustration instead of limitation.

EXAMPLE 1

Preparation of Type I Collagen

The following process can be used to prepare type I collagen. Three hundred grams of bovine tendon is chopped into small pieces of about 0.5 $cm^3$ and mixed with 10 liters of 95% ethanol at 4° C. for 24 hours. Transfer the tendon pieces into 10 liters of 0.5 M acetic acid solution and stir the mixture at 4° C. for 72 hours. Add pepsin (SIGMA P7000, 4000 unit/ml) to the mixture and stir the mixture at 4° C. for 24 hours. Filter the mixture and discard the remnants. Add sodium chloride to the solution and adjust the final concentration to 1.0 M. Mix the solution under magnetic stirring at 4° C. for 30 minutes. Centrifuge the prepared solution at 10,000 g (Beckman Avanti J-20) for 30 minutes and remove the supernatant. Resuspend the pellet by adding 10 liters of 50 mM Tris-HCl solution (pH 7.4) and stir the solution at 4° C. for 30 minutes. Add sodium chloride to a final concentration of 4.0 M. Mix the solution completely at 4° C. for 30 minutes. Remove the supernatant after being centrifuged at 10,000 g for 30 minutes. Resuspend the pellet with 10 liters of 50 mM Tris-HCl solution (pH 7.4), and mix the solution completely at 4° C. for 30 minutes. Add sodium chloride again to the solution until the final concentration is 2.5 M, and stir the solution for 30 minutes at 4° C. Remove the supernatant after being centrifuged at 10,000 g for 30 minutes. Add 5 liters of mixed solution of isopropanol and $H_2O$ (Isopropanol:$H_2O$=1:4) to resuspend the pellet, and mix at 4° C. for 30 minutes under magnetic stirring. Remove the supernatant after being centrifuged at 10,000 g at 4° C. for 30 minutes, and resuspend the pellet with 5 liters of 0.05 M acetic acid solution. Repeat the procedure of centrifugation/resuspension twice. Freeze the solution at −90° C. Lyophilize the solution and obtain the desiccated product of Type I collagen.

Preparation of Drug-Free Biodegradable 3D Porous Collagen/Glucosaminoglycan Scaffold Dissolve 4.8 g of type I collagen, obtained from the process in Example 1 above, in 400 ml of 0.05 M acetic acid. Mix the solution in a water bath at 10° C. under magnetic stirring stepwise from 3,500 rpm for 60 minutes, 7,000 rpm for 30 minutes to 11,500 rpm for 60 minutes. Dissolve 0.48 g of chondroitin-6-sulfate (C-6-S) in 80 ml of 0.05 M acetic acids. Then mix the C-6-S solution with type I collagen solution under magnetic stirring stepwise from 3,500 rpm for 60 minutes, 7,000 rpm for 30 minutes to 11,500 rpm for 60 minutes. Pour the collagen and C-6-S mixture into a 4-liter flask. Vacuum the mixture until the pressure is lower than 30 mtorr and store the mixture at 4° C. Place 160 ml of the cold collagen and C-6-S mixture in a 14 cm×22 cm stainless tray. Lyophilize the collagen and C-6-S mixture at −90° C., until a sheet-like collagen and C-6-S mixture has been obtained. Seal the sheet of collagen and C-6-S mixture in an aluminum-foil bag and polymerize the collagen and C-6-S mixture by exposure to a vacuum at a temperature of 105° C. for 24 hours. Take out the sheets of collagen/C-6-S copolymer from the aluminum-foil bag, and further crosslink by exposure to 254 nm UV for 2 hours each side in a UV crosslinker. Store the 3D porous sheet of collagen/C-6-S copolymer in a dry aluminum-foil bag at 4° C.

The ratio of collagen/glycosamnioglycans in the scaffold can be maintained at 10:1. The difference between the embodiments of the present invention described above and those disclosed in the art is that no further aldehyde cross-linkage has been applied during the scaffold preparation. Therefore, there is no risk of chemical remnants. In addition, the obtained scaffold is much softer, since no secondary chemical cross-linkage has been done during the preparation.

EXAMPLE 2

Measurement of the Static Pressure after being Saturated by Physiological Buffer The structure for modulating intraocular pressure on glaucoma containing 0.25%, 0.5% and 1% collagen/C-6-S copolymers separately are cut into discs with 7, 7.5, 8, 8.5, and 9 mm in diameter and 2 to 3 mm in thickness. Weigh the discs by a scale and take records. Place the discs in 0.1 M PBS until the collagen/C-6-S copolymers are saturated and weigh the discs. Repeat the steps 10 times. Calculate the saturated static pressure of the scaffold per unit area on the basis of the following equation: saturated static pressure of the scaffold (mmHg)=[Weight of the saturated scaffold (mg)−Weight of the dry scaffold (mg)]×0.0736/Area of the scaffold (mm$^2$). Variation of the measurements is evaluated by a t-test.

The saturated static pressure of the scaffold is the maximum anticipating intraocular buffering pressure. The data indicates that the greater the concentration of collagen/C-6-S copolymer in the scaffold is, the greater the saturated static pressure increases (see FIG. 1). This is because collagen molecules have high affinities of binding with $H_2O$. In addition, the data shows that the scaffold with the same concentration of collagen/C-6-S copolymers but different in size has a property where the saturated static pressure is in direct proportion to the size of the area. The result indicates the stable and homogeneous on nature of collagen/C-6-S copolymers. Hence, the scaffold with various concentrations of collagen/C-6-S copolymers and different shapes can be prepared in advance upon different demands.

EXAMPLE 3

Animal Model of the Implantation of the Structure of Controlling Intraocular Pressure in Regulating the Intraocular Pressure on Glaucoma The structure of modulating intraocular pressure on glaucoma of 0.5% collagen/C-6-S copolymer is cut into several identical small discs of 8-mm in diameter and 2-3 mm in thickness. The discs are immersed exhaustively in 0.1 M PBS for 4 to 6 hours to be saturated. Seventeen female New Zealand albino rabbits weighing between 2.5 to 3.5 kg are anesthetized by an intramuscular injection of ketamine (35 mg/kg, BW) and xylazine (5 mg/kg, BVW. All the scaffolds are implanted in the animals' right eyes with their left eyes serving as the surgical sham control. Open the eyelids with a speculum. A wound of approximately 8-10 mm in length is made by ophthalmic scissors on the right eye. The wound is located between the 10 o'clock and 12 o'clock position at a distance of 2 mm away from the corneal-scleral limbus. Separate the conjunctival epithelium and substantia propia to expose the sciera. Build a channel over the trabeculum to connect the anterior chamber and subconjuctival space, wherein implant the scaffold. Seal the wound. To be a surgical sham control, the same surgical procedures are done on the left eyes without the scaffold implantation.

EXAMPLE 4

Histological Evaluation after the Structure of Controlling Intraocular Pressure Implantation 17 implanted rabbits are sacrificed by excess anesthetics of ketamine (2×35 mg/kg BW) and xylazine (2×5 mg/kg, BW) on day 3, 7, 14, 21, and 28 after implantation. Quickly remove the eyes including the eyelids and fix them in 4% formaldehyde overnight. The implant and underlying scleral bed is dissected, dehydrated, and embedded in paraffin. Sections are cut by a microtome at 7 μm and stained with H&E (hematoxylin and eosin) for general histological observation, and Masson trichrome stain to assess collagen deposition and remodeling. Additional tissue sections are used for the α.-SMA (α.-smooth muscle actin) immunocytochemistry to identify the distribution of myofibroblasts. The procedures of H&E stain, Masson's trichrome stain, and α-SMA immunocytochemistry are described below:

Evaluation of the General Histology by H&E Stain after Implanting the Structure of Modulating Intraocular Pressure on Glaucoma:

Deparaffin the tissue sections by heating the slides in 56° C. for 10 minutes and immersing in 100% xylene for 3 minutes (repeat 3 times). Transfer the slides in 100% ethanol for 2 minutes (repeat 3 times) and rehydrate sequentially to 90%, 80%, 70%, and 50% ethanol for 3 minutes each step. Stain the slides in hematoxylin solution for 10 minutes and remove the excessive dye in distilled water for 5 minutes (repeat 2 times). Then place the slides in eosin solution for 20 seconds. Wash the slides in distilled water to remove the excessive dye for 5 minutes (repeat 2 times). The stained tissue is dehydrated by sequential 50%, 70%, 80%, 90%, 100% ethanol for 10 seconds each. After the secondary treatment in 100% ethanol, place the slides in the 100% xylene for 10 seconds (repeat 3 times). Cover the slides with Permount or Polymount, and observe under light microscopy.

Figure 2A:
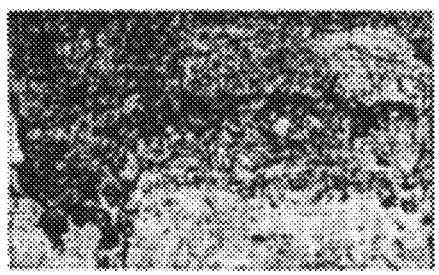
FIGS. 2A, 2C, 2E, and 2G, show the results from the implanted groups.
Figure 2B:
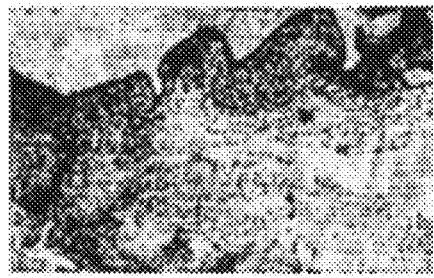
FIGS. 2B, 2D, 2F, and 2H show the results from the operating sham groups.

Wound areas of both implanted and un-implanted eyes evidence a typical acute inflammatory response at day 3 and day 7 after surgery. A mass of immunogenic cells aggregate, consisting of occasional elongated cells of fibroblasts, macrophages, and different types of lymphocytes. Collagens secreted by fibroblasts are deposited adjacently to the wound. The inflammatory cells and fibroblasts infiltrate into the area of the inner one third to one half of the scaffold adjacent to the sclera (FIG. 2a, 2b). Although the implanted scaffold is gradually degraded after 7 days, the remaining portion is visible. The remaining 3D porous structure for the regenerated cells distributes along the irregular pores. Fibroblasts predominantly extend beyond the pores and connect directly to the epithelium layer of the sclera. The immune responses have decreased gradually from day 14 and subside completely by day 21 after surgery. There is no difference in the immune response and in the subsiding time between the implanted and un-implanted wounds. The result indicates that the scaffold induced no additional immune response. Moreover, a loosely organized network is left with the invasion of scattered regenerated cells and secreted collagens on the implanted areas after the scaffold is degraded. Oppositely, the un-implanted surgery areas are occupied by a packed array of collagen fibers, and the conjunctiva of the un-implanted left eye is much thicker.

Identification of Collagen by Masson's Trichrome Stain

The tissue slides are deparaffinized in 100% xylene solution for 5 minutes (repeat 2 times) and rehydrated in 100%, 100%, 95%, 80%, 70% of ethanol in-and-out for 10 to 20 times. The tissue slides are mordanted in Bouin's Solution (Sigma M HT10-32) at 56° C. for one hour and then at room temperature overnight in a hood. Wash the tissue slides in running tap water to remove yellow color from tissue sections and rinse briefly in distilled water. Stain the tissue sections in Weigert's Iron Hematoxylin Solution (Sigma HT10-79) for 10 minutes. Wash in running tap water for 10 minutes and rinse in distilled water. Place the tissue slides in freshly prepared phosphomolybdic/phosphotungstic acid solution for 10-15 minutes. The fresh phosphomolybdic/phosphotungstic acid solution can be prepared by mixing phosphomolybdic acid (Sigma HT15-3) and 10% (w/v) phosphorungstic acid (Sigma HT15-2) in a 1:1 ratio by volume. Stain the tissue sections in Aniline Blue Solution for 5 minutes and rinse briefly in distilled water. Place the tissue slides in 1% glacial acetic acid solution for 3-5 minutes and dehydrate by sequential exposure to 70%, 80%, 90%, and 100% of ethanol for 10 seconds separately. After the secondary treatment in 100% ethanol, the tissue slides are transferred to 100% xylene solution for 10 seconds (repeat three times). Coverslip the tissue slides with Permount or Polymount, and observe under microscopy.

Figure 2C:
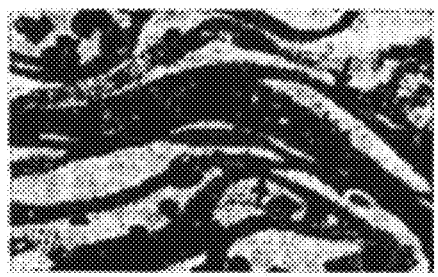
Figure 2D:
Figure 2E:
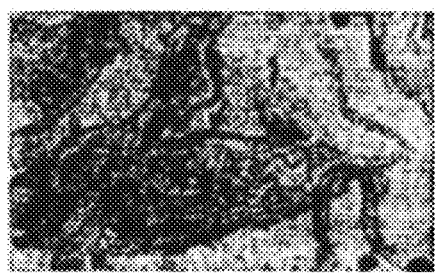
Figure 2F:
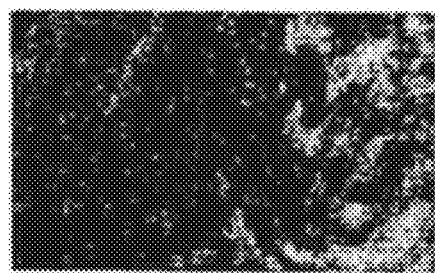
Figure 2G:
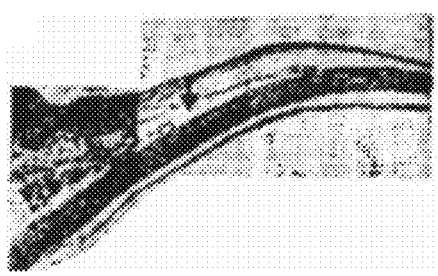
Figure 2H:
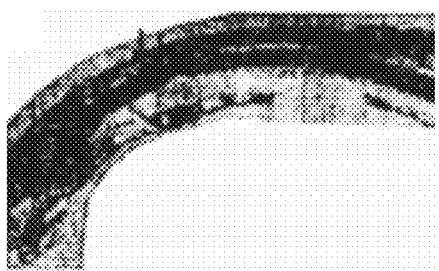

Stained collagen fibers appear in the implanted and un-implanted wound areas on day 3 after surgery. In tissue sections obtained from the 14th day after surgery, the scar forms in the un-implanted wound areas with a much more densely packed array of collagen fibers (FIG. 2c, 2d). The scar tissue continually develops up to day 28 after surgery (FIG. 2g, 2h). As compared with the results of immunostain of α.-SMA on day 14 after surgery, there are many more myofibroblasts aligning compactly in the un-implanted wound areas (FIG. 2e, 2f). The observation confirms that the scaffold prevents scar formation.

Identify the Distribution of Active Myfibroblast by α-SMA Immunocylochemistry

Deparaffin the tissue slides by heating at 56 ° C. for 10 minutes and dip the tissue slides into 100% xylene for 3 minutes (repeat 3 times). Transfer the tissue slides in 100% ethanol for 3 minutes (repeat 2 times) and expose sequentially to 90%, 80%, 70%, and 50% of ethanol for 3 minutes each step. Wash the tissue slides in 0.1 M PBS for 3 minutes (repeat 2 times), and place the tissue slides in 3% $H_2O$ at room temperature for 15 minutes. Wash the tissue slides in 0.1 M PBS containing with 0.2% Triton-X 100 (PBST) for 2-3 minutes (repeat 3 times). Block the non-specific bindings with 10% fetal bovine serum (FBS) in 0.1 M PBST at room temperature for 25 minutes. Incubate the tissue slides with α-SMA (Neomarkers) monoclonal antibody in a dilution of 1:500 at 4° C. overnight. After washing the tissue slides in PBST for 2-3 minutes (repeat 3 times), incubate the tissue slides with biotinylated anti-mouse/rabbit IgG (DAKO $LSAB2^R$ system, visualizing kits available from Dako North America, Carpinteria, CA) in a dilution of 1:400 for 15 minutes at room temperature. Wash the tissue slides in PBST for 2-3 minutes (repeat 3 times). Drop streptavidin-HRP (DAKO $LSAB2^R$ system) onto the tissue sections and incubate at room temperature for 15 minutes. Wash the tissue slides with PBST for 2-3 minutes (repeat 3 times). Conduct the chromogen (DAKO $LSAB2^R$ system) reaction at room temperature for 10 minutes. Wash the tissue slides with PBST for 2-3 minutes (repeat 3 times). Counterstain with Hematoxylin solution for 30 seconds and wash in PBS for 3 minutes (repeat 3 times), followed by distilled water for 5 minutes (repeat 2 times). Cover the slides with glycerol gel (DAKO) at 56° C. and observe under microscopy. The materials in the DAKO $LSAB2^R$ system described above include biotinylated link and streptavidin-HRP. The biotinylated link comprises biotin labeled affinity isolated goat anti-rabbit and goat anti-mouse immunoglobulins in phosphate buffered saline (PBS), containing stabilizing protein and 0.015 mol/L sodium azide. The streptavidin-HRP comprises streptaviin conjugated to horseradish peroxidase in PBS containing stabilizing protein and anti-microbial agents.

In the unimplanted eye, immunostain of α-SMA reveals that numerous myofibroblasts aligned parallel to the sclera surface until day 14 after surgery, and the compactly aggregated collagen fibers secreted by myofibroblasts resulted in wound contraction. In contrast, only a few scattered myofibroblasts distributed in the implanted areas of the implanted eyes. They adhere randomly to the remaining scaffold and the wound area surroundings (FIG. 2e, 2f). As a result, wound contraction seldom happens in the implanted eyes. The wound contracts obviously on the day 21 after surgery because of the aggregation of collagen fibers in the subepithelial space and the contraction of the myofibroblasts adjacent to the wound of the un-implanted eyes. The subepithelial space is consequently smaller or collapsed. In comparison with the implanted eyes, the larger subepithelial space is due to the random distribution of collagen fibers and myofibroblasts as well as the degradation of collagen/C-6-S copolymers. Observation on day 28 after surgery shows that in implanted eyes the number of fibroblasts and myofibroblasts decreased and the stroma was replaced by the collagen fibers at the implanted wound areas. The collagen fibers align in a random orientation. In contrast, an obvious scar formation appears in the un-implanted eyes (FIG. 2g, 2h).

EXAMPLE 5

The Change of the Intraocular Pressure (IOP)

The intraocular pressure of the female New Zealand albino rabbits in Example 4 is measured with tonopen. Preceding measurement, the rabbits are anesthetized by an intramuscular injection with a half dosage of ketamine (35 mg/kg, BW) and xylazine (5 mg/kg, BW) before measurement on days 3, 7, 14, 21, and day 28. The same measurement is adopted before the rabbits are sacrificed for further morphological studies. Compared with the pressure before implantation, the changing rate of intraocular pressure is obtained by the formula below: 1 The IOP changing rate (%)=IOP before implantation−IOP after implantation IOP before implantation×100%.

Figure 3:
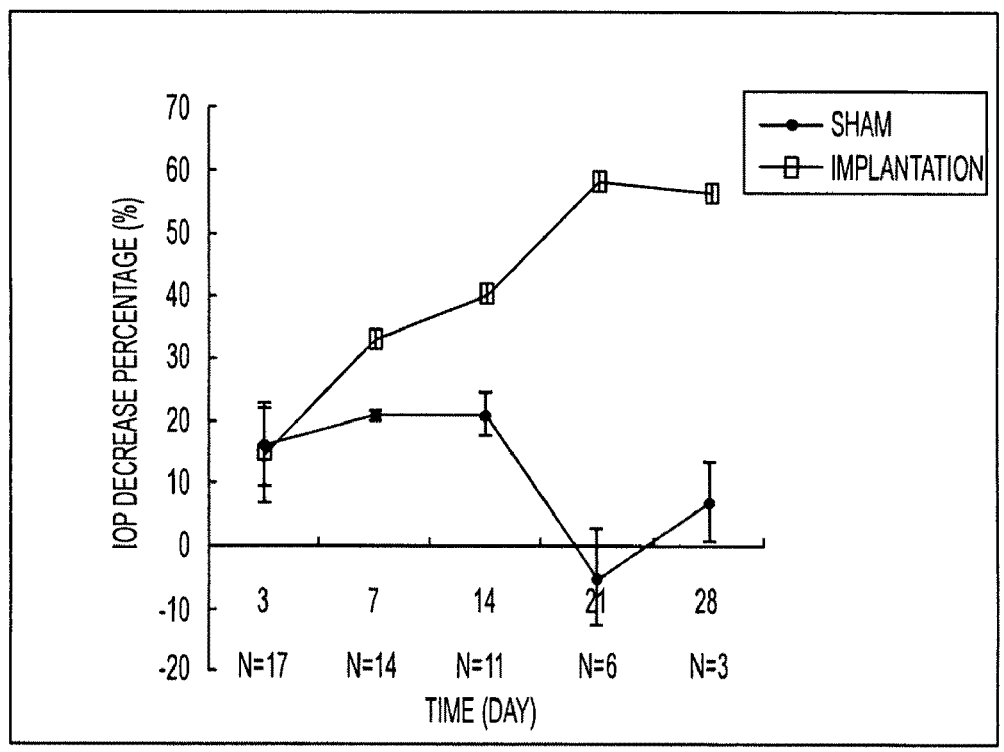
FIG. 3 indicates the development of the intraocular pressure after scaffold implantation.

In the un-implanted eyes, IOP decreases about 16% immediately after the channel connected to the anterior chamber is built and remains constant until 14 days, and then gradually increases, returning to the value measured before the surgery. In the situation of implanted eyes, IOP decreases about 14% immediately after the channel is built and then further decreases to 33% at day 7 after surgery. During tissue regeneration, the IOP decreases as well, and reaches to about 55% at day 28 after surgery (FIG. 3). The results temporally fit the morphological observation.

EXAMPLE 6

Collagen Matrix

Figure 4:
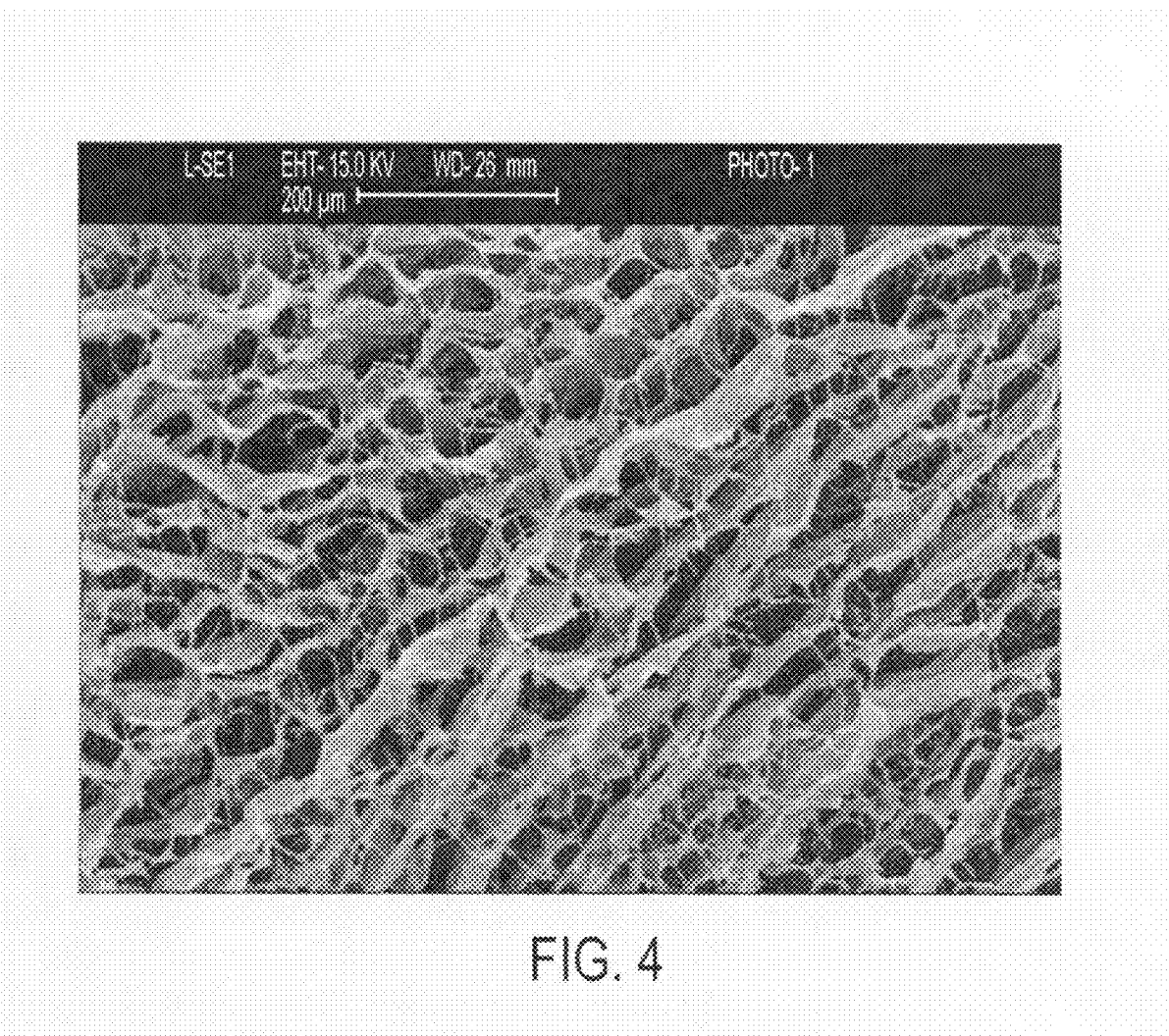
FIG. 4 shows an electronic microscopy image of collagen matrix.

By scanning electron microscopy, the collagen matrix consisted of a diffusely porous material. The pore size of the collagen matrix ranged from 20 μm to 200 μm (the percentage of collagen/glycosaminoglycan is about 1%) (FIG. 4). Since pore size relates to the percentage of copolymers, the pore size of the scaffold with lower percentage of copolymers is bigger than 200 μm.

Based on previous findings, the collagen matrix provides a physiological structure for tissue regrowth (epithelium, stroma and vessels), inducing a conjunctival wound to heal in a more physiological than pathological process. In the case of filtering surgery in this rabbit model, a one-month degradation period was sufficient to create a prominent bleb compared with that in the control group. The conjunctval stroma after use the scaffold of this invention became one part of the aqueous system with a prominent bleb, and the collagen dispersed inside the aqueous humor is indistinguishable from the surrounding collagen with no scar formation.

The collagen implant offers a potential alternative to antifibrotic agents, producing more loosely organized bleb tissue than a bleb created without antifibrotic agents and yet more abundant tissue than one created with antifibrotic agents. This new approach using a degradable collagen implant to normalizing filtering surgical wound healing offers potential benefits both from the point of physics and of physiology.

Under progressively increasing weight on top PBS soaked scaffold, the pressure generally elevated with a reduction in height of scaffold. However, the pressure dropped in a small range of the soaked PBS scaffold when the strain reached around 3.2. At the same time, PBS was released from the scaffold prominently (the percentage of collagen/glycosaminoglycan is about 1% and ratio of collagen and glycosaminoglycan is 24:1) (FIG. 11). Strain is the change in length/original length. When the matrix is compressed by external force, it will become more rigid and become more difficult to deform. However, once the external exceed its stiffness (around 1.12 to 1.19 Kpa), the PBS-soaked scaffold suffers extreme crush in structure which triggering the flow-out of the PBS retained in the scaffold and hence the distorted scaffold can not continue to maintain its 3D structure and the saturated statistic pressure thereof.

The scaffold can resolve both the problem of applying pressure on the scleral flap and that of maintaining a functional bleb until healing is complete.

Hematoxylin-Eosin Staining

Wound areas of both implanted and control eyes showed a typical acute inflammatory response at days 3 and 7 after surgery. Elongated fibroblasts, macrophages, and different types of lymphocytes aggregated on the surface of implant. The implanted matrix began to degrade after 7 days postoperatively.

The ingrowing cells distributed throughout the porous pattern of the implant but less densely than on the surface. The inflammatory responses decreased gradually from day 14 and subsided completely by day 21 after surgery in the control group and day 28 as the implant degraded completely.

Figure 5:
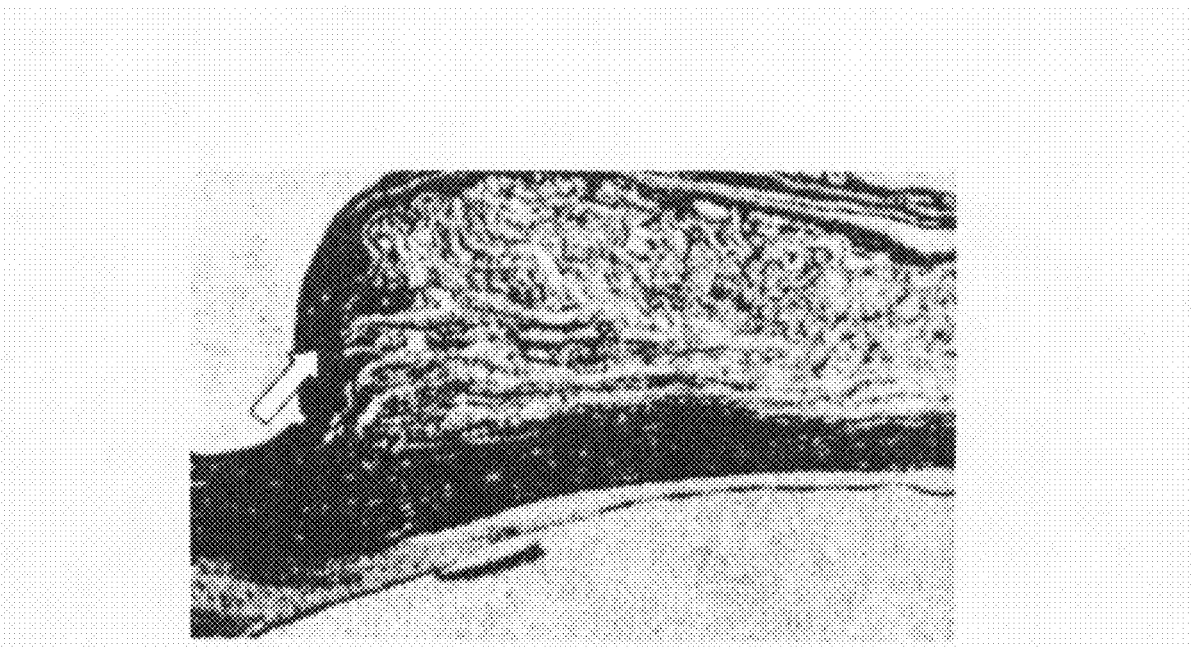
FIG. 5 shows an intact implant in the subconjunctival space with cells (white arrow) migrating on its surface. The nuclei are stained brown (Masson Trichrome stain, 20×, Day 7).
Figure 6:
FIG. 6 shows a partially degraded implant (white arrow) inside a prominent bleb. Cells are present inside the implant, as opposed to the region where the implant has degraded, in which only collagen remains (black arrow) (Masson Trichrome stain, 20×, Day 14).

In the control eyes, immunostaining of α-SMA showed numerous myofibroblasts aligned parallel to the sclera surface until day 14 after surgery, and compactly aggregated collagen fibers secreted by myofibroblasts. In contrast, the implanted eyes showed fewer myofibroblasts, which adhered randomly to the remaining matrix and the surrounding wound area (FIG. 5). During the period of degradation of the implant, the bleb space remained prominent (FIG. 6).

Figure 7:
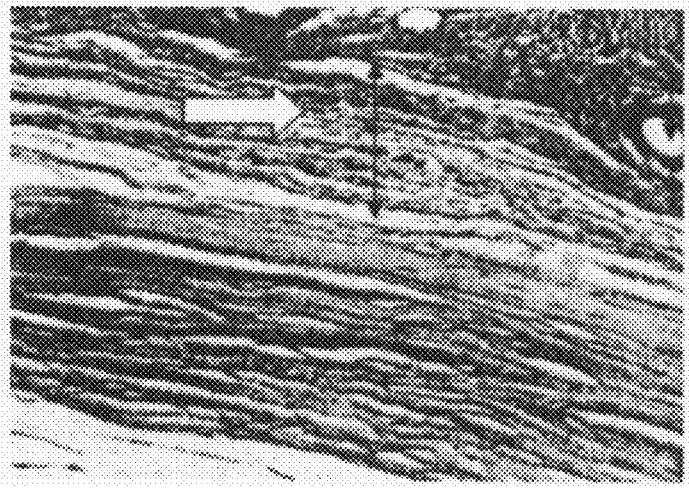
FIG. 7 shows linear collagen (white arrow) deposited inside the collapsed bleb (long black arrow) in a control group. Sclera was seen in this view. 10-0 nylon (20-30 um diameter, short black arrow) at right upper corner (Masson Trichrome stain, Day 21).
Figure 8:
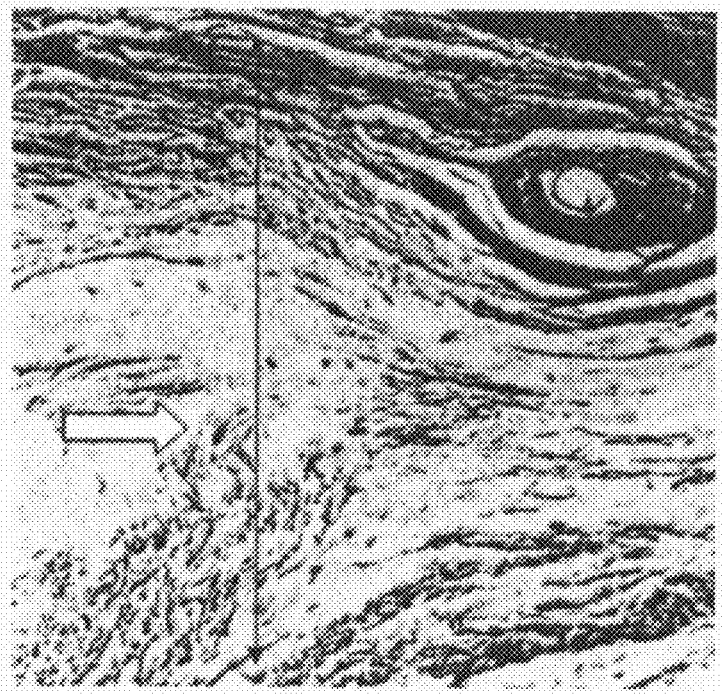
FIG. 8 shows randomized collagen (white arrow) deposited in a prominent bleb (long black arrow) in the implanted group (depth indicated by longer black arrow, 16 times the diameter of a 10-0 nylon indicated by shorter black arrow). No sclera was seen in this view. 10-0 nylon (20-30 um diameter, black arrow) was located at right upper corner (Masson Trichrome stain, Day 21).
Figure 9:
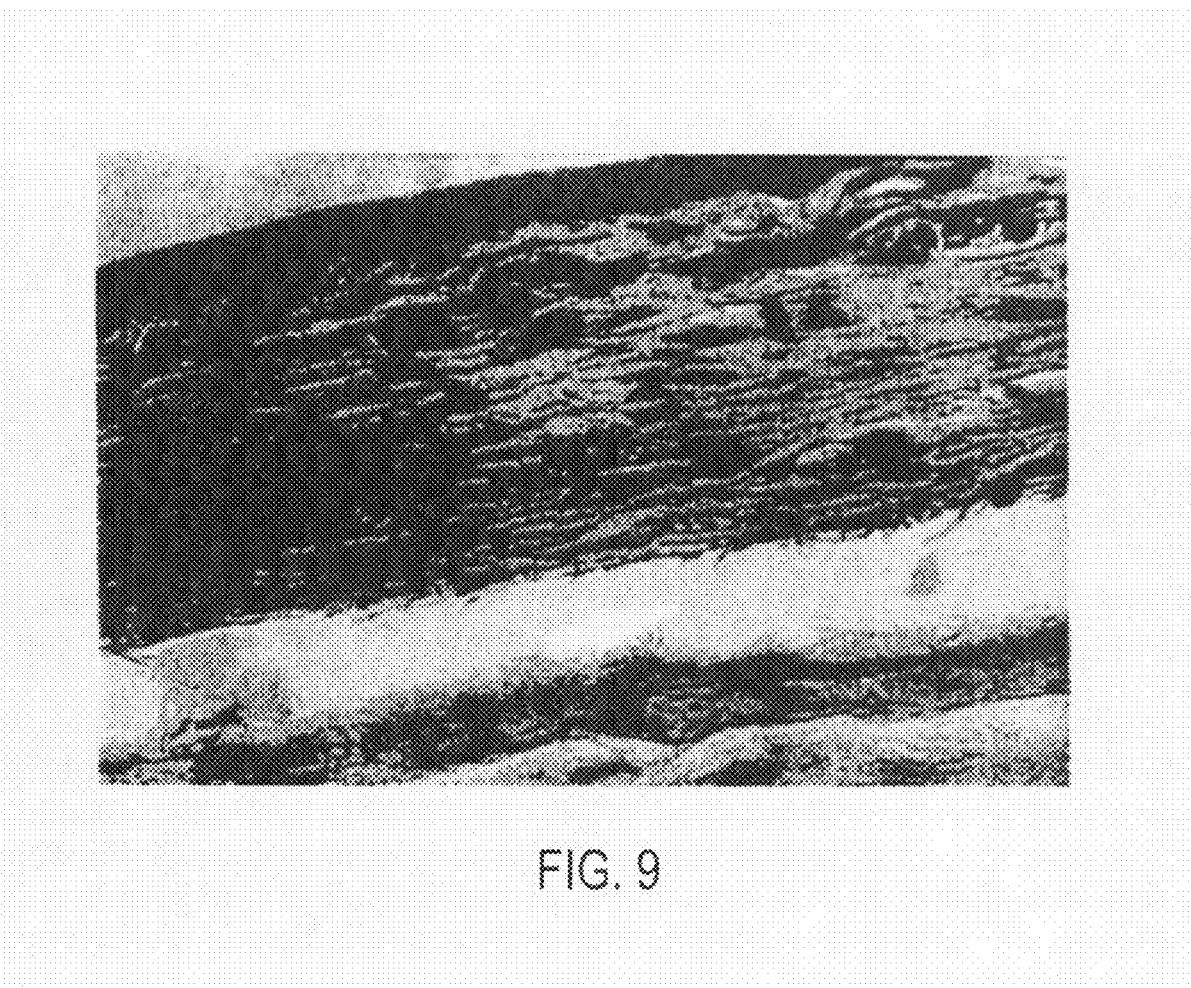
FIG. 9 shows the morphological evaluation before scaffold implantation.
Figure 10:
FIG. 10 shows the morphological evaluation before scaffold implantation.

On postoperative day 21, diminished bleb size in the control eyes was even more pronounced, combined with the aggregation of collagen fibers in the subconjunctival space (FIG. 7). Control eyes 28 days after surgery showed a diminished bleb space with dense linear collagen filling in the subconjunctival space. The implanted group on postoperative day 21 had a prominent bleb with some collagen dispersed inside the subconjunctival space and the structured implant no longer visible (FIG. 8) Comparison of the depths of the blebs revealed that the blebs of the implanted group were 5 to 6 times deeper than those of the control group (the diameter of a 10-0 nylon is used here as a unit).

The current 3-D collagen matrix has been designed to achieve two goals: provide a physiological environment to control cell in growth and provide a physical weight on the scleral flap to prevent shallow anterior chambers. Two parameters, concentration and temperature, relate to the inner structure of the matrix. In this example, a 1% collagen/glycosaminoglycan copolymer is adopted and underwent a freeze-drying process in this example.

Based on previous findings, the collagen matrix provides a physiological structure for tissue regrowth (epithelium, stroma and vessels), inducing a conjunctival wound to heal in a more physiological than pathological process. In the case of filtering surgery in this rabbit model, a one-month degradation period was sufficient to create a prominent bleb compared with that in the control group. The conjunctval stroma after use the scaffold of this invention became one part of the aqueous system with a prominent bleb, and the collagen dispersed inside the aqueous humor is indistinguishable from the surrounding collagen with no scar formation.

The collagen implant offers a potential alternative to antifibrotic agents, producing more loosely organized bleb tissue than a bleb created without antifibrotic agents and yet more abundant tissue than one created with antifibrotic agents. This new approach using a degradable collagen implant to normalizing filtering surgical wound healing offers potential benefits both from the point of physics and of physiology.

EXAMPLE 7

The reasons why a bleb may fail are well discussed in the field of subconjunctival and slceral flap fibrosis. Most studies focus on the proliferation of fibroblasts and try to inhibit it. However tissue engineering offers another approach to avoid fibrosis; not by inhibiting the proliferation of fibroblasts but by instead guiding the pattern of migration and collagen deposition by fibroblasts. However, the natural wound's ability to diminish the surface of wound repair is another key related the successful rate of filtering surgery. In this example, we calculate the stiffness of the collagen scaffold by the rebounding effect post compressive on top of it and the size of bleb post implantation.

During the process of wound healing, myofibroblasts play an important role in contraction. The physiologic meaning of the contraction is to reduce the area of new tissue to cover the wound defect. However, in the filtering surgery, this phenomenon increases the chance of bleb failure by contract the depth and size of the reservoir (as show in FIG. 6). On the other point, the process of wound healing won't last forever. At the period of inflammation, wounds go forward for wound closing and become mature, i.e., less cellularity and more extracelluar matrix. That is, persistent foreign body is not necessary to maintain the bleb in a mature wound. By the concept stated above, a biodegradable material which can offer the stiffness to against the purse effect of myofibroblast and last until the period of inflammation pass, can improve the outcome of filtering surgery.

The result of this example shows most cells were on the surface of the scaffold without interfere the inner structure of the scaffold (pore size). In fact, the size of the bleb can be maintained by the scaffold during the period of wound healing without collapse (as show in FIG. 7, there is one interesting find in the histologic picture is one layer of aqueous cover the scaffold make the dense cellularity outside the scaffold which may contribute the maintain of the size of the bleb.

The wound created during the filtering surgery over conjunctiva is the process of extend of the bleb by scissor and suture of the conjunctival wound. The procedure may induce the subconjunctival storma inflammation and transformation of the fibroblasts into myofibroblasts. By the effects of the contraction of the myofibroblasts, bleb size decreased gradually and may become bleb total gone eventually. This may happen more prominent in the high risk patient who may have longer inflammatory course. Without early inflammatory control or inhibition of proliferation of fibroblasts, high failure rate is observed in clinic. Even though the effect of antimetabolic medicine can get some good early postoperative result, long term complications still worry surgeons.

A successful filtering surgery should have the following attributes: First, the conjunctiva should works functionally with normal structure; Second, the bleb can be maintained with a stable physiologic condition; and Third, the scleral tunnel can still patent after the wound become mature. Therefore a biodegradable scaffold, which can offer the stiffness to prevent the purse effect, can make a for a successful filtering surgery.

For some non-biodegradable implant, they can supply a persistent size of implant itself with consistent bleb size. Actually, the reservoir is the implant itself not the bleb. The function of the bleb is the outer conjunctiva layer function as a dynamic drainage of aqueous humors. However the persistent foreign body effect may make the wound become inflammatory even the wound subside for a certain period. Decasualization of the bleb is one of the results of chronic inflammation reaction. A safer way for long term effect is to create a new environment of drainage system between anterior camber and conjunctival drainage system without any foreign body as a successful traditional filtering surgery dues. How to improve the results of traditional filtering surgery esp, in the high risk cases is the goals of the present invention. A functional conjunctiva can be regenerated by implant a collagen matrix in a conjunctival wound was proved (2000 IOVS Hsu). A scaffold, which can against the contraction of wound healing and maintain the size of reservoir, offer a better chance of good IOP control and long term effect. Tissue engineering can be a next potential method in improving the results of filtering surgery.

Although the present invention has been described with reference to the preferred embodiments, it will be understood that the invention is not limited to the details described thereof. Various substitutions and modifications have been suggested in the foregoing description, and others will occur to those of ordinary skill in the art. Therefore, all such substitutions and modifications are intended to be embraced within the scope of the invention as defined in the appended claims. All documents cited herein are incorporated in their entirety by reference.

We claim:

1. A scaffold comprising at least two polymers in an amount that produces: a saturated static pressure of about 0.5 mmHg to about 5.5 mmHg, after saturation in saline; and a stiffness of about 0.5 KPa to about 2 KPa after saturation in saline, wherein a first polymer is selected from the group consisting of collagen or gelatin and a second polymer is selected from the group consisting of chondroitin-6-sulfate, chondrotin-4-sulfate, heparin, heparan sulfate, keratan sulfate, dermatan sulfate, chitin, and chitosan.

2. The scaffold of claim 1, wherein said scaffold has a stiffness of 1 KPa to 1.6 KPa.

3. The scaffold of claim 1, wherein one of the polymers is type I collagen.

4. The scaffold of claim 1, wherein the scaffold has a pore size of about 10 μm to about 300 μm.

5. A kit comprising the scaffold of claim 1.

6. The scaffold of claim 1, wherein the saline is 0.1 M PBS.

7. The scaffold of claim 1, wherein the saturated static pressure is about 1.75 mmHg to about 3.5 mmHg.

8. The scaffold of claim 7, wherein said scaffold has a stiffness of 1 K.Pa to 1.6 KPa.

9. A scaffold comprising collagen and a glycosaminoglycan, wherein the scaffold has a pore size of about 10 μm to about 300 μm and a saturated static pressure of about 1 mmHg to about 4 mmHg and a stiffness of about 1 KPa to about 1.6 KPa after saturation in saline.

10. The scaffold of claim 9, wherein the pore size is about 20 μm to about 200 μm and wherein the scaffold has a saturated static pressure of about 1.75 mmHg to about 3.5 mmHg.

11. A kit comprising the scaffold of claim 10.

12. The scaffold of claim 11, wherein the saline is 0.1 M PBS.

* * * * *

UNITED STATES PATENT AND TRADEMARK OFFICE
CERTIFICATE OF CORRECTION

PATENT NO. : 7,544,368 B2  Page 1 of 1
APPLICATION NO. : 11/806442
DATED : June 9, 2009
INVENTOR(S) : Hsu et al.

It is certified that error appears in the above-identified patent and that said Letters Patent is hereby corrected as shown below:

In the Specification, in the Detailed Description of the Invention:

In column 5, line 56, replace ~~glycosaminoglycan:collagen~~ with collagen:glycosaminoglycan.

Signed and Sealed this

Twenty-third Day of March, 2010

David J. Kappos
*Director of the United States Patent and Trademark Office*